United States Patent
Duclos (10) Patent No.: US 12,102,636 B2
(45) Date of Patent: Oct. 1, 2024

(54) ADMINISTRATION OF ANTIPSYCHOTICS

(71) Applicant: Medtronic, Inc., Minneapolis, MN (US)

(72) Inventor: Brian A. Duclos, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 101 days.

(21) Appl. No.: 17/173,841

(22) Filed: Feb. 11, 2021

(65) Prior Publication Data

US 2022/0249472 A1 Aug. 11, 2022

(51) Int. Cl.
*A61K 31/4985* (2006.01)
*A61K 31/095* (2006.01)
*A61M 5/142* (2006.01)

(52) U.S. Cl.
CPC ........ *A61K 31/4985* (2013.01); *A61K 31/095* (2013.01); *A61M 5/14276* (2013.01); *A61M 2005/14208* (2013.01)

(58) Field of Classification Search
CPC ................................................ A61K 31/4985
See application file for complete search history.

(56) References Cited

U.S. PATENT DOCUMENTS

| | | |
|---|---|---|
| 4,692,147 A | 9/1987 | Duggan |
| 5,711,316 A | 1/1998 | Elsberry et al. |
| 10,653,713 B2 | 5/2020 | Thakker et al. |
| 2005/0090548 A1* | 4/2005 | Hildebrand .......... A61K 31/195 514/561 |
| 2009/0131857 A1* | 5/2009 | Geiger ................. A61K 31/145 424/94.1 |

FOREIGN PATENT DOCUMENTS

| | | | |
|---|---|---|---|
| WO | WO-2009014762 A1 * | 1/2009 | ............. A61K 31/00 |
| WO | 2019/178484 | 9/2019 | |
| WO | 2020/047241 | 3/2020 | |
| WO | 2020/047407 | 3/2020 | |
| WO | 2020/047408 | 3/2020 | |

OTHER PUBLICATIONS

Holl et al., "The spinal canal: from imaging anatomy to diagnosis", J Radiol. Sep. 2010 (Year: 2010).*
"SynchroMed II Drug Infusion Pump", Medtronic, Feb. 15, 2020 (Year: 2020).*
Sullivan et al. "Atypical Antipsychotics and Inverse Agonism at 5-HT2 Receptors", Curr Pharm Des. 2015 (Year: 2015).*
"CAPLYTA (Lumateperone) capsules", FDA, Dec. 23, 2019 (Year: 2019).*
"Lumateperone Tosylate", Sigma-Aldrich, Aug. 25, 2020 (Year: 2020).*
Gerner et al., "Doxepin by Topical Application and intrathecal routes in Rats", Anesthesia and Analgesia, pp. 283-287, Jan. 2006 (Year: 2006).*
Nakai et al., "Effects of intrathecal administration of atypical antipsychotics in a rat model of trigeminal neuropathic pain", Acute and Chronic Pain Management, Jun. 2013 (Year: 2013).*
Flavio Guzman, "Mechanism of Action and Pharmacodynamics of Olanzapine", Psychopharmacology institute, Dec. 13, 2014 (Year: 2014).*
"Aripiprazole", DrugBank Online, Oct. 20, 2020 (Year: 2020).*
"Intrathecal Administration", Wikipedia, Oct. 2, 2015 (Year: 2015).*
Snyder et al., Functional profile of a novel modulator of serotonin, dopamine, and glutamate neurotransmission?, Psychopharmacology, 232, 2015, pp. 605-621.

* cited by examiner

Primary Examiner — John S Kenyon
Assistant Examiner — Gillian A Hutter
(74) Attorney, Agent, or Firm — Mueting Raasch Group (57) ABSTRACT

A system includes: a liquid formulation comprising an antipsychotic agent and an implantable infusion device. The implantable infusion device includes a reservoir, an outlet in communication with the reservoir, a drive mechanism configured to cause liquid formulation in the reservoir to be delivered to the outlet, and control electronics coupled to the drive mechanism. The control electronics are programmed with instructions that cause the liquid formulation to be delivered from the reservoir to the outlet at a flow rate of less than 500 microliters per hour for a period of time sufficient to reach a therapeutically effective steady state concentration in a subject's cerebrospinal fluid (CSF) if the liquid is delivered to a CSF-containing space of a subject.

19 Claims, 7 Drawing Sheets

ADMINISTRATION OF ANTIPSYCHOTICS

FIELD

This disclosure relates to methods and systems for delivering antipsychotic agents, such as selective 5-HT2a antagonists, to a brain by administration to cerebrospinal fluid (CSF), such as intrathecal (IT) administration.

BACKGROUND

A variety of agents have been administered to CSF, such as through intracerebroventricular (ICV) or IT bolus infusion. Typically, these agents are administered acutely through a single, bolus infusion at flow rates in the range of about 0.5 to 12 ml/min. At such high delivery rates, the agents can achieve wider distribution within the central nervous system (CNS), albeit transiently.

However, at lower flow rates, such as less than 1 ml/day, studies report that the distribution of the agent in the CSF is limited. For example, one study reported the distribution of a small molecule agent within the CSF following IT infusion at a rate of 20 microliters per hour was limited to less than 5 cm of the spinal cord relative to the infusion site.

In many situations and for many reasons, it would be desirable to administer an agent at a low flow rate to a subject's CSF; e.g. when using a chronically implanted infusion device, but achieve broad distribution of the agent in the subject's CNS. U.S. Pat. No. 10,653,713 B2 discloses broad CSF distribution of an agent is achievable at flow rates less than 500 microliters per hour.

Selective 5-hydroxytryptamine receptor 2a ("5-HT2a") antagonists, such as Caplyta® (lumateperone tosylate), are a newer class of selective antipsychotic agents with diminished side effects over current standard of care treatments. Although efficacious CNS concentrations may be achieved by oral administration, work is ongoing to develop long-acting subcutaneous, as well as transdermal applications, to achieve a stable steady state concentration.

Such efforts are being undertaken, at least in part, because patients that exhibit psychosis tend to have poor compliance with taking oral medications. For example, roughly one-third of patients suffering from schizophrenia are non-compliant with oral medication dosing regimens, either intentionally or non-intentionally. The nature of the disease, the ramifications of non-adherence on patient safety, and the societal costs are compelling reasons to develop alternative routes of administration and administration schemes to administer antipsychotic agents, such as selective 5-HT2a antagonists.

SUMMARY

The present disclosure describes methods and systems for delivering antipsychotic agents directly to a subject's CSF. The agents may be delivered at a flow rate suitable to achieve therapeutically effective steady-state concentrations. Preferably, the flow rate is suitable to achieve broad distribution within the CSF.

The antipsychotic agents may be administered by an implantable infusion device. The implantable infusion device may have a reservoir configured to hold a sufficient volume of therapeutic fluid comprising an antipsychotic agent to deliver therapeutically effective concentrations for a prolonged duration. For example, the concentration of the antipsychotic agent in the therapeutic fluid, the volume of the reservoir, and the flow rate may be configured to deliver the therapeutic fluid for a week or more, or a month or more.

With such extended delivery and maintenance of therapeutically effective concentrations, treatment may be more effective. This may lead to better patient compliance associated with the refill of the reservoir each week, each month, every two months, or the like, as needed.

The implantable infusion device may comprise suitable electronics to monitor the reservoir fill level. If the therapeutic fluid is nearly depleted, the device may alert the patient, a health care provider, or both the patient and the health care provider that the reservoir should be refilled. If the reservoir is not refilled or of the patient does not timely schedule a refill, the health care professional may contact the patient to follow up, which may result in improved compliance and continued therapy.

In one aspect, the present disclosure describes a method comprising: (i) selecting a subject to which administration of an antipsychotic agent is desired; and (ii) administering a liquid formulation comprising the antipsychotic agent directly to cerebrospinal fluid (CSF)-containing space of the subject at a flow rate of less than 500 microliters per hour. The liquid formulation is administered for a period of time sufficient to reach a therapeutically effective steady state concentration in CSF of a brain of the subject.

The subject may be suffering from one or more of schizophrenia, bipolar disorder, and major neurocognitive disorder. The major neurocognitive disorder may be associated with Alzheimer's disease.

The antipsychotic agent may comprise a 5-HT2a antagonist.

The liquid formulation may be introduced into the CSF-containing space via a catheter. The catheter may have a delivery region through which the antipsychotic agent is configured to exit, and the delivery region may be positioned in a lumbar, thoracic, or cervical region of the subject's spinal intrathecal space, the cerebral ventricles, the subdural space (for example overlying the cerebral cortex), or any other place where CSF may be safely accessed. Preferably, the CSF-containing space is selected from the group consisting of lumbar intrathecal space, thoracic intrathecal space, and cervical intrathecal space.

The catheter may be operatively coupled to an implantable infusion device.

In another aspect, the present disclosure describes a system comprising: (i) a liquid formulation comprising an antipsychotic agent; and (ii) an implantable infusion device. The implantable infusion device comprises (a) a reservoir configured to house the liquid formulation, (b) an outlet in fluid communication with the reservoir, (c) a drive mechanism configured to control the rate at which the liquid formulation is delivered to the outlet from the reservoir, and (d) electronics operably coupled to the drive mechanism. The electronics are programmed with instructions that cause the liquid formulation to be delivered from the reservoir to the outlet at a flow rate of less than 500 microliters per hour for a period of time sufficient to reach a therapeutically effective steady state concentration in a subject's cerebrospinal fluid (CSF) if the liquid is delivered to a CSF-containing space of a subject.

The antipsychotic agent may comprise a 5-HT2a antagonist.

The details of one or more aspects of the disclosure are set forth in the accompanying drawings and the description below. Other features, objects, and advantages of the techniques described in this disclosure will be apparent from the description and drawings, and from the claims.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

The following description illustrates various embodiments. It is to be understood that other embodiments are contemplated and may be made without departing from the scope or spirit of the present invention. Thus, the following description is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

As used herein, the singular forms "a", "an", and "the" encompass embodiments having plural referents, unless the content clearly dictates otherwise.

As used herein, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to".

As used herein, "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

As used herein, the terms "treat" or the like means alleviating one or more symptom, slowing the progression, preventing, attenuating, or curing the treated disease.

As used herein, "disease", "disorder", "condition" or the like, as they relate to a subject's health, are used interchangeably and have meanings ascribed to each and all of such terms.

As used herein, "subject" means a mammal to which an agent is administered for the purposes of treatment or investigation. Preferably, the mammal is a human.

As used herein, a "liquid formulation" of a compound is a composition that contains the compound and that is liquid at 20 degrees Celsius and at 37 degrees Celsius.

As used herein, "therapeutically effective" concentration of a therapeutic agent is a concentration of the therapeutic agent capable of treating a disease. A therapeutically effective concentration of a therapeutic agent in a subject's CSF is a concentration in the CSF that is effective to treat a disease in the subject, such as a disease of the brain.

As used herein, a "steady state" concentration is a concentration that does not vary by more than 25 percent over an extended duration, such as over 24 hours. Preferably, a steady state concentration does not vary by more than 20 percent, or by more than 15 percent, over 24 hours.

As used herein, "broad distribution" of a therapeutic agent means that the therapeutic agent is distributed generally throughout most, if not all, of the region of interest. For example, if brain CSF is the region of interest, then the therapeutic agent will be generally distributed throughout the CSF compartments in and surrounding the brain. If the CSF in general is the region of interest, the therapeutic agent delivered to a specific location of the CSF is considered to be broadly distributed in the CSF if, after delivery, the molecule is present throughout the CSF.

As used herein, "an antipsychotic agent" is a compound capable of, or used for, treating psychosis. Antipsychotic agents may be useful for treating diseases that are not associated with psychosis.

As used herein, "psychosis" is a symptom of one or more psychiatric, neurodevelopmental, neurologic, and medical conditions that impairs a person's ability to distinguish what is real from what is not real. Psychosis is used herein interchangeably with psychotic disorder. A person suffering from psychotic disorder may exhibit delusions, hallucinations, or both delusions and hallucinations. Hallucinations are a sensory perception in the absence of a corresponding external or somatic stimulus. Examples of hallucinations include visual hallucinations, auditory hallucinations, tactile hallucinations, olfactory hallucinations, gustatory hallucinations, and the like. Delusions are fixed false beliefs. Delusions are based on incorrect inferences about reality external to, or about, oneself and maintained firmly despite the presentation of evidence that obviously and incontrovertibly contradicts the belief. Psychosis may be diagnosed as described in Diagnostic and Statistical Manual of Mental Disorders (5th ed) ("DSM-5"), American Psychiatric Association (2013). Some diseases or disorders for which psychosis may be a symptom include schizophrenia, bipolar disorder, and major neurocognitive disorder.

As such herein, "schizophrenia" is a disease in which a person exhibits one or more of delusions, hallucinations, and disorganized speech and may also exhibit gross disorganization, catatonic behavior, or negative symptoms. Schizophrenia may be diagnosed as indicated in DSM-5. Antipsychotic agents may be used to treat schizophrenia.

As used herein, "biopolar disorder" is a disease in which a person has experienced at least one episode of mania or hypomania. Psychosis may, or may not, be a symptom of bipolar disorder. Bipolar disorder, which includes bipolar I disorder, bipolar II disorder, and cyclothymic disorder, may be diagnosed as indicated in DSM-5. Antipsychotic agents may be used to treat bipolar disorder, whether associated with psychosis or not.

As used herein, "major neurocognitive disorder" is a disorder in which a person exhibits a substantial cognitive decline from a previous level of performance and the cognitive deficits interfere with independence. Major neurocognitive disorder may be referred to as dementia. Major neurocognitive disorder may be associated with Alzheimer's disease. Major neurocognitive disorder may be diagnosed as indicated in DSM-5. Antipsychotic agents may be used to treat major neurocognitive disorder, whether associated with psychosis or not.

As used herein, "5-HT" means 5-hydroxytryptamine, which also may be referred to as serotonin.

As used herein, "5-HT2a" means 5-hydroxytryptamine receptor 2a. 5-HT2a is one of three known receptors in the 5-HT2 receptor subfamily. A protein sequence of the human 5-HT2a receptor has a UniProtKB accession number of P-28223 (available at world wide web at uniprot.org/uniprot/P28223#sequences, last visited 8 Feb. 2021). A genetic sequence of the human 5-HT2a receptor has a GeneCard ID of GC13M046831 (available at world wide web at genecards.org/cgi-bin/carddisp.pl?gene=HTR2A, last visited 9 Feb. 2021). A number of variants have been reported and are considered to be 5-HT2a receptors.

As used herein, a "5-HT2a antagonist" is a compound that occupies the 5-HT2a receptor but does not activate the receptor. A 5-HT2a antagonist may reduce or prevent the ability of agonists to activate the receptor. Lumateperone tosylate is an example of a selective 5-HT2a receptor antagonist.

As used herein, a "selective" 5-HT2a antagonist is an antagonist that selectively binds to the 5-HT2a receptor relative to other receptors of the 5HT2 receptor subfamily. For example, a selective 5-HT2a antagonist may have a binding affinity to the 5-HT2a receptor that is 10 times or more, such as 100 times or more, greater than the binding affinity of the selective 5-HT2a antagonist for the other 5-HT2 receptor subfamilies. In other words, the dissociation constant (Kd) of the selective 5-HT2a antagonist may be 10-fold, or 100-fold, less for the 5-HT2a receptor than for the 5-HT2b receptor or for the 5-HT2c receptor.

Reference herein to a compound, such as a therapeutic agent, includes reference to salts, free-bases, free-acids, polymorphs, and isomers of the therapeutic agent.

As used herein, "control electronics" means hardware, software, firmware, and combinations thereof that control operation of one or more component, module, unit, or system. Control electronics may be provided in any suitable form and may, for example, include a controller or a memory and a controller. The controller may include one or more of an Application Specific Integrated Circuit (ASIC) state machine, a digital signal processor, a gate array, a microprocessor, or equivalent discrete or integrated logic circuitry. Control electronics may include memory that contains instructions that cause one or more components of the control electronics to carry out a function or aspect of the control electronics. If implemented in software, functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer). Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of a described function.

The present disclosure relates to, among other things, achieving broad distribution of antipsychotic agents in cerebrospinal fluid (CSF) of a subject by delivering the antipsychotics in a liquid formulation at a flow rate of less than 500 microliters per hour and for a duration that is up to or longer than that required to achieve steady state concentrations of the antipsychotic agent in the CSF. The duration required to achieve steady state concentrations in the CSF may, in some embodiments, be approximated based on a known turnover rate of CSF.

Figure 1:
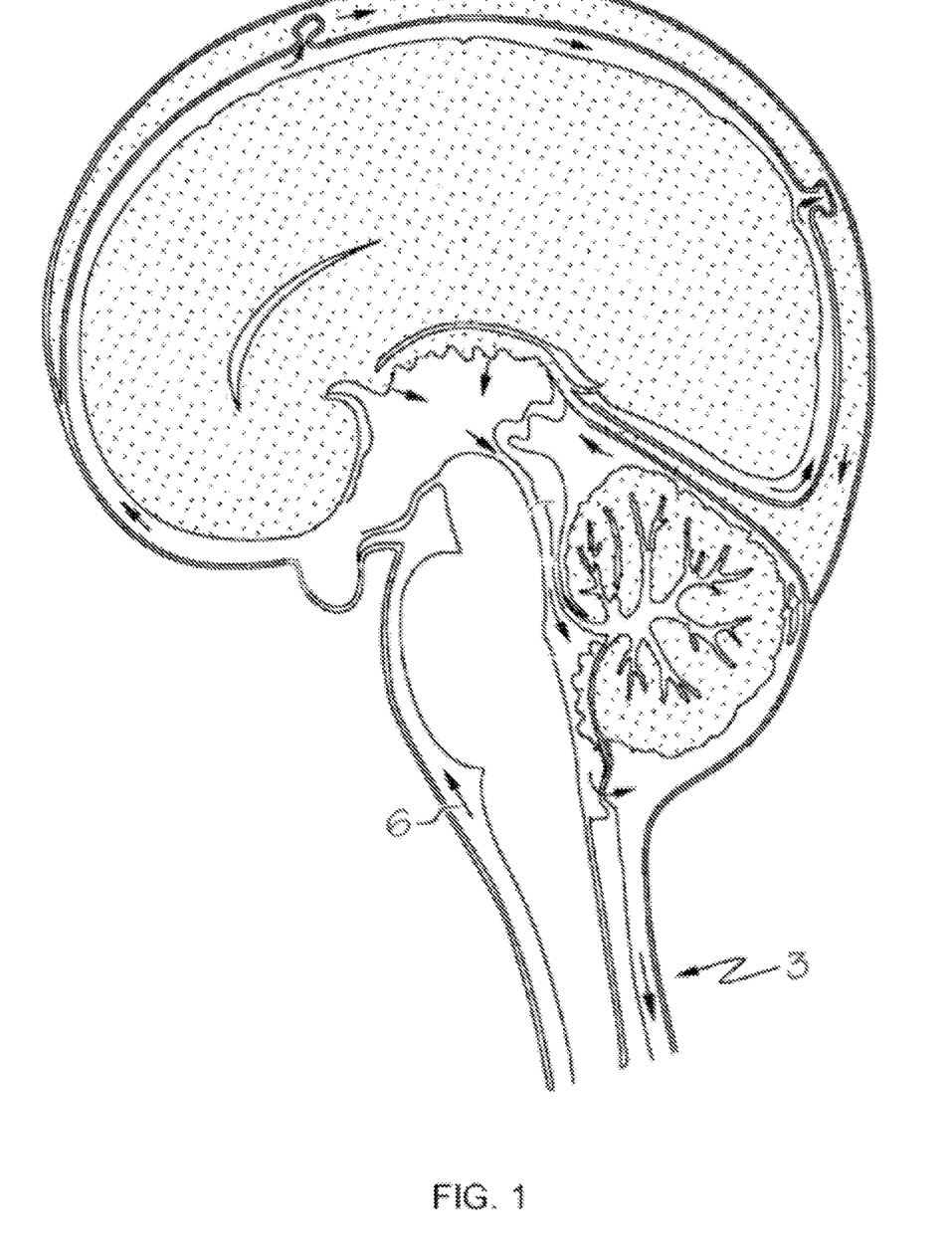
FIG. 1 is a schematic drawing of a section of a brain and portions of a spinal cord showing CSF flow.

According to various embodiments, a liquid formulation containing an antipsychotic agent may be delivered directly to cerebrospinal fluid 6 of a subject. Referring to FIG. 1, CSF 6 exits the foramen of Magendie and Luschka to flow around the brainstem and cerebellum. The arrows within the subarachnoid space 3 in FIG. 1 indicate cerebrospinal fluid 6 flow. The subarachnoid space 3 is a compartment within the central nervous system that contains CSF 6. The CSF 6 is produced in the ventricular system of the brain and communicates freely with the subarachnoid space 3 via the foramen of Magendie and Luschka. A liquid formulation including antipsychotic agent may be delivered to CSF 6 of a subject anywhere that the CSF 6 is accessible. For example, the liquid formulation may be administered intrathecally (e.g., at a lumbar, sacral, thoracic or cervical level or into the cisterna magna), intracerebroventricularly, or the like. In some embodiments, the fluid composition is administered subdurally, for example by delivery of the liquid formulation to the CSF over the cortical convexities of the brain.

Any suitable antipsychotic agent may be included in the liquid formulation delivered to the CSF. The antipsychotic agent may be of any suitable size. As demonstrated in U.S. Pat. No. 10,653,713, which is incorporated herein by reference in its entirety, small molecules (less than 5 kDa) and large molecules (greater than 5 kDa) may be broadly distributed in CSF of the brain when administered intrathecally to the CSF and delivered at rates of less than 500 microliters per hour. In some embodiments, the antipsychotic agent has a molecular weight of 200 grams/mole or less. In some embodiments, the antipsychotic agent has a molecular weight in a range from 200 grams/mole to 600 grams/mole. In some embodiments, the antipsychotic agent has a molecular weight of 600 grams/mole or more. For molecules having molecular weights less than 5,000 grams/mole, the molecular weight may be determined by adding the standard atomic masses (in grams/mole) of the constituent atoms.

Examples of antipsychotic agents that may be included in a liquid formulation for delivery to CSF include typical antipsychotic agents and atypical antipsychotic agents. Typical antipsychotic agents may be referred to as neuroleptics or major tranquilizers. Typical antipsychotic agents are typically dopamine receptor antagonists. Atypical antipsychotic agents may be referred to as second generation antipsychotic agents. Atypical antipsychotic agents may be dopamine receptor antagonist that are selective for the dopamine-2 (D2) receptor, may be serotonin (5-HT) antagonists, or may have D2 and 5-HT antagonist properties. Preferably, the antipsychotic agent is a 5-HT2a antagonist. The 5-HT2a antagonist may also have dopamine receptor, such as D2 receptor, antagonist properties. Preferably, the 5HT2a antagonist is a selective 5-HT2a receptor antagonist. The selective 5-HT2a antagonist may also be an antagonist for one or more dopamine receptors.

Examples of typical antipsychotic agents that may be included in a liquid formulation for delivery to the CSF include chlorpromazine, thioridazine, trifluoperazine, fluphenazine, perphenazine, loxapine, molindone, thiothixene, haloperidol, and pimozide.

Examples of atypical antipsychotic agents that may be included in a liquid formulation for delivery to the CSF include aripiprazole, asenapine, brexpiprazole, cariprazine, clozapine, iloperidone, lumateperone, lurasidone, olanzapine, paliperidone, pimavanserin, quetiapine, risperidone, and ziprasidone. Preferably, the antipsychotic agent is lumateperone. For example, the antipsychotic agent may be lumateperone tosylate.

The antipsychotic agents may be formulated into any suitable liquid formulation for delivery to the CSF. The formulation may include the antipsychotic agent and a variety of other pharmaceutically acceptable components. See Remington's Pharmaceutical Science (15th ed., Mack Publishing Company, Easton, Pa. (1980)). The preferred form may depend on the intended application. The formulations may also include, depending on the formulation desired, pharmaceutically acceptable, nontoxic carriers or diluents, which are defined as vehicles commonly used to formulate pharmaceutical compositions for animal or human administration. In most cases, the diluent is selected so as not to adversely affect the activity of antipsychotic agent. Examples of such diluents are distilled water, physiological phosphate-buffered saline, artificial cerebrospinal fluid, citrate buffered saline, Ringer's solutions, dextrose solution, and Hank's solution.

Typically, the liquid formulations are formed as injectable compositions. Injectable compositions include solutions, suspensions, dispersions, or the like. Injectable solutions, suspensions, dispersions, or the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Proper fluidity of solutions, suspensions or dispersions may be maintained, for example, by the formation of liposomes, by the maintenance of the desired particle size, in the case of dispersion, or by the use of nontoxic surfactants.

The prevention of microorganisms can be accomplished by heat sterilization or filter sterilization, whichever is compatible with the molecule and formulation being used. Isotonic agents such as sugars, buffers, or sodium chloride may be included. Solubility enhancers may be added.

In various embodiments, the final formulation is adjusted to have a pH between 4 and 9, between 5 and 8, or between 5.5 and 7. The pH of the composition may be adjusted with a pharmacologically acceptable acid, base, or buffer. Hydrochloric acid is an example of a suitable acid, and sodium hydroxide is an example of a suitable base. The hydrochloric acid or sodium hydroxide may be in any suitable form, such as a IN solution.

The liquid formulation containing the antipsychotic agent may be used for therapeutic, diagnostic or investigatory purposes. In various embodiments, a liquid formulation contains an amount of the antipsychotic agent effective to treat a disease or to allow meaningful study of a subject to which the liquid formulation is administered at a particular flow rate. The effective amount of the antipsychotic agent to be administered may vary depending on the agent itself and the disease to be treated. The amount may also vary depending on the subject to which it is administered and the location of administration (e.g., IT vs. ICV).

The liquid formulation containing the antipsychotic agent be administered to the CSF in any suitable manner. In various embodiments, a system including an infusion device is used to deliver a liquid formulation containing an antipsychotic agent to subject. The system may further include a catheter operably coupled to the infusion device. The infusion device may include a drive mechanism or pump, such as a piston pump, peristaltic pump, positive pressure reservoir, or the like. Non-limiting examples of infusion devices include osmotic pumps, fixed-rate pumps, programmable pumps and the like. Each of the aforementioned pump systems contains a reservoir for housing the liquid formulation and an outlet in fluid communication with the reservoir. The catheter may be operably coupled to the outlet. The catheter includes one or more delivery regions, through which the fluid may be delivered to one or more target regions of the subject. The infusion device may be implantable or may be placed outside the body via an externalized catheter outside the body, external to the subject. Alternatively, an implanted port that is in direct communication with a CSF compartment via a catheter can be accessed on an intermittent basis and drug infused over the desired duration using an external pump delivering the drug at an appropriate rate as described herein.

The liquid formulation may be administered at any suitable rate to the subject's CSF to achieve broad distribution. In many embodiments, the composition is administered at a rate of less than 500 microliters per hour. For example, the composition may be administered at a rate of less than 200 microliters per hour or between about 4 microliters per hour and 100 microliters per hour or between about 2 microliters per hour and 25 microliters per hour. It will be understood flow rates per hour may be converted to flow rates per minute, per second, per day, etc. using appropriate conversion factors and that, when properly converted, such flow rates are considered equivalent.

The infusion device may be configured to deliver the liquid formulation at any suitable rate. By way of example, the infusion device may include electronics configured to control the rate at which the liquid formulation may be delivered from the reservoir to the outlet. In embodiments, the electronics are programmed with instructions that cause the liquid formulation to be delivered at a desired rate.

As demonstrated in U.S. Pat. No. 10,653,713, a combination of factors, including the time to allow the infused test article to reach steady state, infusion target site, infusion flow rate, and the molecular weight of the agent, may be adjusted to achieve predetermined distribution of the agent in the CNS. CSF volume and turnover may be relevant to extent and location of distribution of an agent administered to the CSF. In a human, the average volume of CSF is about 125 milliliters and the average turnover rate is about 20 milliliters per hour.

In some embodiments, a liquid formulation comprising an antipsychotic agent may be delivered to a subject, such as a human, at a flow rate of 2 milliliters per day, 3 milliliters per day, 4 milliliters per day, 5 milliliters per day, 10 milliliters per day, 20 milliliters per day, or the like.

The CSF volume and turnover rate may be relevant to determining an appropriate concentration of antipsychotic agent in the liquid formulation to achieve a therapeutically effective concentration at the selected flow rates.

In some embodiments, the volume of the liquid formulation administered to the CSF of a subject in a day is limited to avoid adverse effects such as hydrocephalus. For example, the volume of liquid formulation delivered per day may be 25% or less of the CSF volume of the subject, 20% or less of the CSF volume of the subject, 15% or less of the CSF volume of the subject, 10% or less of the CSF volume of the subject, 5% or less of the CSF volume of the subject, or 2% or less of the CSF volume of the subject. By way of example, 25% of the CSF volume of a typical adult human is about 30 ml, and 10% of the CSF volume is about 12.5 ml.

To achieve a suitable flow rate to achieve broad distribution while conserving on the amount or volume delivered, a therapeutic or diagnostic composition may be delivered to a subject's CSF in pulsatile or episodic manner, as a controlled and programmed therapy rather than at a constant rate. For example, a therapeutic agent may be administered at a sufficiently high flow rate and duration to achieve desired distribution within the CNS, and then the flow rate would be reduced to a very low level for a prolonged period of time (days to weeks) to conserve drug and also maintain patency of the catheter. This pattern may be repeated on a chronic basis. It will be understood that nearly any other pulsatile dosage regimen may be employed and that the regimens discussed above are merely examples.

In some embodiments, between about 10 ml and 100 ml of a therapeutic or diagnostic composition is delivered to the CSF of a subject per month; e.g., about 20 ml/month or about 40 ml/month. A desired pulsatile delivery regimen may thus be calculated based on this desired volume. By way of example, if a flow rate of 2.4 ml per day is suitable to achieve desired CSF distribution and if it is desired to deliver 20 ml or less per month, the composition may be delivered at a rate of about 0.0017/min for one minute, every four minutes (or 15 times an hour). This would result in delivery of about 0.0255 ml/hour, 0.612 ml/day, or about 18.36 ml/month (assuming 30 days in a month). The rate, duration, and frequency of delivery may be modified as desired to achieve desired distribution and desired delivery volumes.

Preferably, the rate, duration, and frequency of delivery are determined such that an appropriate steady state concentration of antipsychotic agent is achieved at desired CSF location. For example, if an antipsychotic agent is delivered at an intrathecal location with the intention of having an effect at the brain, it would be desirable for steady state concentrations of the antipsychotic agent in the CSF at, for example, the ventricles to be sufficiently high to be effective for treating a disease. It will be understood that the CSF turnover rate and the tendency for the agent to diffuse out of the CSF may be accounted for in determining appropriate rates, durations, and frequencies of delivery, as well as concentrations of therapeutic agent.

Figure 2:
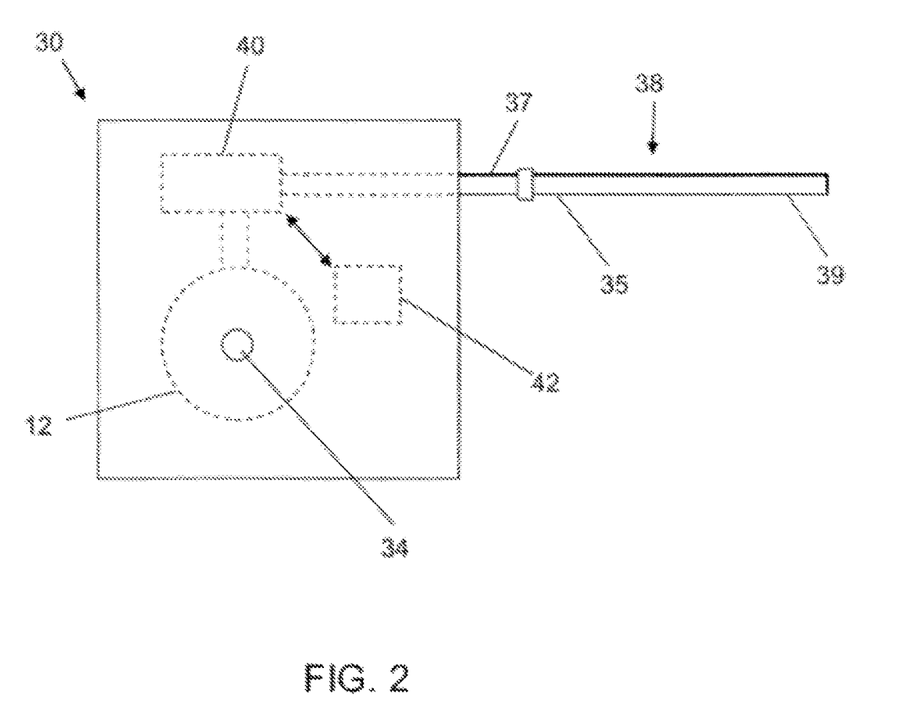
FIG. 2 is a schematic drawing of a side plan view showing some internal components (dashed lines) of a representative infusion device system.

To assist in obtaining such dosage regimens, an infusion system may be employed. An example of an infusion system that may be employed is shown in FIG. 2. The system includes an infusion device 30 having a reservoir 12 for housing a fluid composition and a pump 40 operably coupled to the reservoir 12. The system further includes a catheter 38 having a proximal end 35 coupled to the infusion device 30 and a distal end 39 configured to be implanted in a target location of a subject. Between the proximal end 35 and distal end 39 or at the distal end 39, the catheter 38 has one or more delivery regions (not shown), such as openings, through which the fluid composition may be delivered. The infusion device 30 may have a port 34 into which a hypodermic needle can be inserted to inject the composition into the reservoir 12. The infusion device 30 may have a catheter port 37, to which the proximal end 35 of catheter 38 may be coupled. The catheter port 37 may be operably coupled to reservoir 12. The infusion device 30 may be operated to discharge a predetermined dosage of the pumped fluid into a target region of a subject at a predetermined rate. The infusion device 30 may contain a microprocessor 42 or similar electronics that can be programmed to control the amount and rate of fluid delivery. The programming may be accomplished with an external programmer/control unit via telemetry. With the use of a programmable infusion device 30, dosage regimens may be programmed and tailored for a particular subject. Additionally, different dosages can be programmed for different combinations of fluid compositions. Those skilled in the art will recognize that a programmable infusion device 30 allows for starting conservatively with lower doses and adjusting to a more aggressive dosing scheme, if warranted, based on safety and efficacy factors when used for therapeutic purposes.

Figure 3:
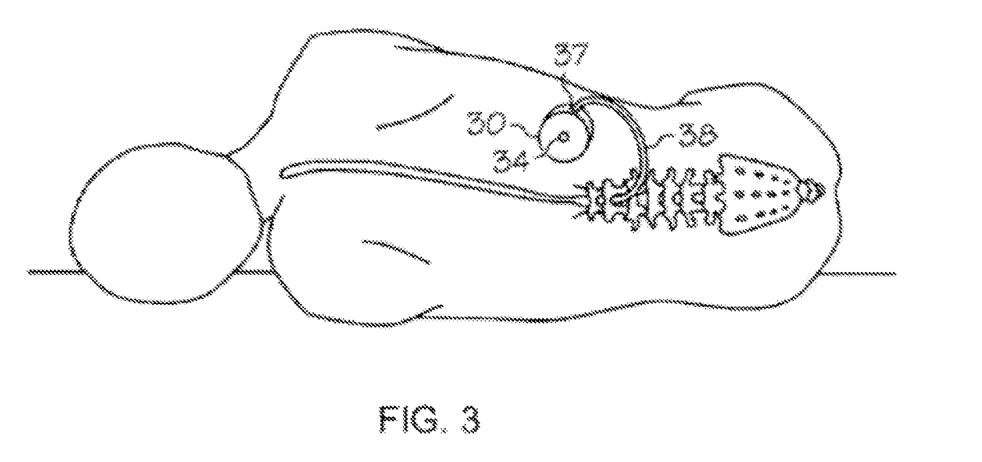
FIG. 3 is a schematic drawing of a view of an infusion device and associated catheter implanted in a subject.

FIG. 3 illustrates an example of an infusion system configured for intrathecal delivery of a liquid formulation comprising an antipsychotic agent. As shown in FIG. 3, a system or device 30 may be implanted below the skin of a patient. Preferably the device 30 is implanted in a location where the implantation interferes as little as practicable with activity of the subject in which it is implanted. One suitable location for implanting the device 30 is subcutaneously in the lower abdomen. In various embodiments, catheter 38 is positioned so that the distal end 39 of catheter 38 is located in the subarachnoid space of the spinal canal such that a delivery region (not shown) of catheter is also located within the subarachnoid space.

In many embodiments, a liquid formulation containing an antipsychotic agent is administered intrathecally at a low flow rate to achieve distribution of the molecule in the brain. Intrathecal (IT) administration provides several advantages to administration directly to the brain or ICV administration. Primarily, IT administration allows one to avoid placement of a catheter or cannula through parenchymal tissue of the brain to reach a desired location or the cerebral ventricle. Accordingly, the subject to which the antipsychotic agent is delivered is spared a great deal of risk and discomfort with IT delivery relative to ICV delivery. Further, the time involved with surgical procedures for IT delivery of an antipsychotic agent is significantly less than for ICV delivery.

However, in some embodiments, a liquid formulation containing an antipsychotic agent is delivered intraparenchymally (IP) or ICV. For ICV delivery, a catheter may be operably coupled to the infusion device and a delivery region of the catheter may be placed in the cerebral ventricle.

Figure 4:
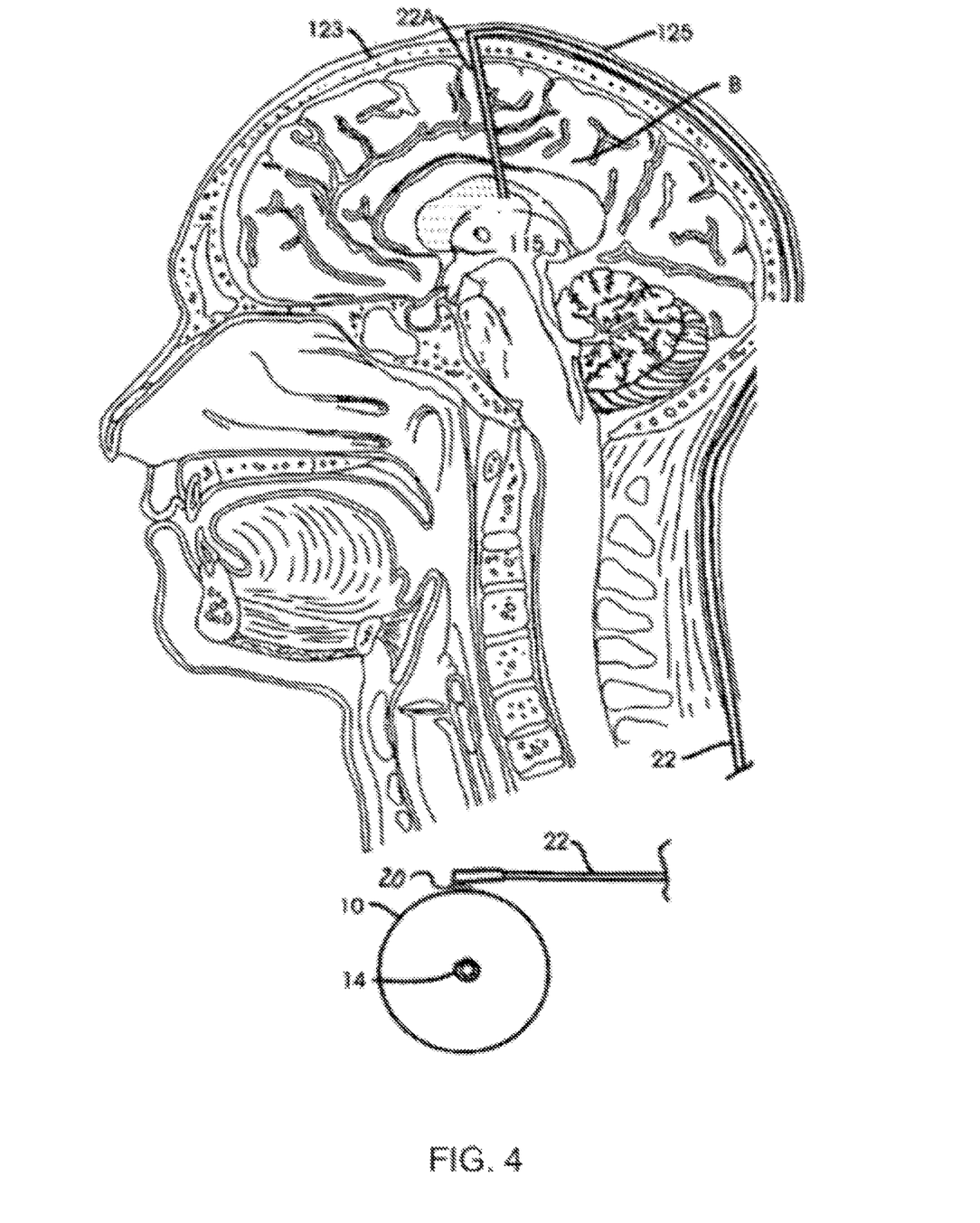
FIG. 4 is a schematic drawing of a view of a section of a subject showing an implanted infusion device and associated implanted catheter.

One suitable system for administering a therapeutic agent to the brain is discussed in U.S. Pat. No. 5,711,316 (Elsberry), which is incorporated herein by reference in its entirety. Referring to FIG. 4, a system or infusion device 10 may be implanted below the skin of a subject. The device 10 may have a port 14 into which a hypodermic needle may be inserted through the skin to inject a quantity of a liquid formulation comprising the antipsychotic agent. The liquid formulation is delivered from device 10 through a catheter port 20 into a catheter 22. Catheter 22 is positioned to deliver the agent to a cerebral ventricle 115 in the brain (B). Device 10 may take the form of the like-numbered device shown in U.S. Pat. No. 4,692,147, which is hereby incorporated by reference in its entirety, may take the form of a SynchroMed II infusion device (Medtronic, Inc.), or may take the form of any currently available or future developed infusion device. In the depicted embodiment, the distal end of catheter 22 terminates in a cylindrical hollow tube 22A having a distal end implanted in the ventricle 115 by conventional stereotactic surgical techniques. Tube 22A is surgically implanted through a hole in the skull 123 and catheter 22 is implanted between the skull and the scalp 125 as shown in FIG. 4. Catheter 22 may be coupled to implanted device 10 in the manner shown or in any other suitable manner.

Figure 5:
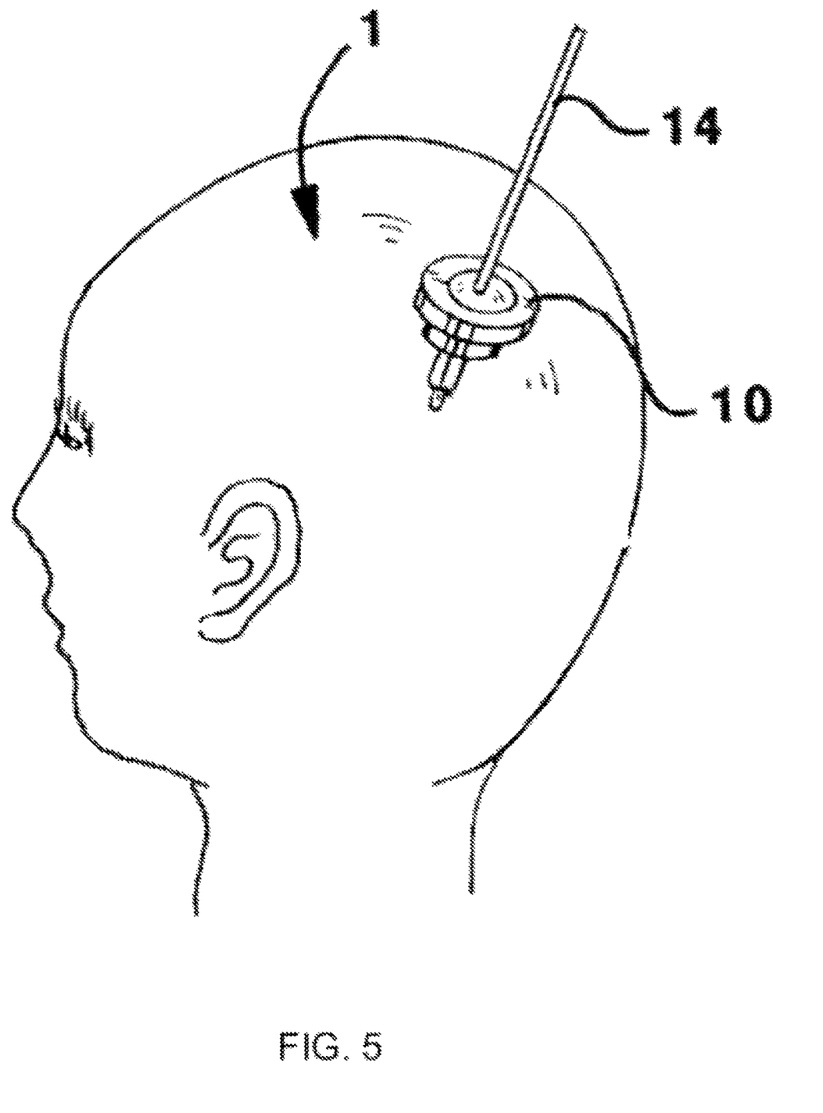
FIG. 5 is a schematic drawing of a view showing an injection port in the environment of a subject.

Referring to FIG. 5, an antipsychotic agent may be delivered to a subject's CSF via an injection port 10 implanted subcutaneously in the scalp of a patient 1, e.g., as described in U.S. Pat. No. 5,954,687, which is hereby incorporated herein by reference in its entirety, or otherwise known in the art. A guide catheter 10 may be used to guide an infusion catheter through port 10 to a target location. Of course, an infusion catheter may be directly inserted through port 10 to the target location. Such ports 10 may also be employed to deliver the molecule intrathecally.

Any other known or developed implantable or external infusion device or port may be employed.

An implantable medical device suitable for delivering a liquid formulation comprising an antipsychotic agent to the CSF of a subject may be capable of determining the fill level of a reservoir of the device and alerting the subject in which the device is implanted, a health care provider, or both the subject and the health care provider when the volume of the liquid formulation in the reservoir is low or depleted. Reservoir fill level may be determined in any suitable manner. For example, fill level can be determined by control electronics of the device by determining the amount of liquid formulation delivered based on flow rate and time and subtracting from the full reservoir volume. The device may have components as described in U.S. Pat. No. 8,708,959 or 8,083,730, each of which are hereby incorporated herein by reference in their entirety, and may determine fill level as described in U.S. Pat. No. 8,708,959 or 8,083,730.

When notified of the low reservoir fill level, the subject may schedule a refill of the reservoir. If the subject does not schedule a refill in a timely manner, the health care provider may contact the subject. Such notification and follow up may result in improved compliance and continuity of treatment.

The implantable medical device may alert the subject or the healthcare provider of a low reservoir fill level in any suitable manner. The device may communicate with an external patient personal device, such as a smart phone, tablet, patient programmer, computer, or the like. The device may contact the health care provider through the internet or other suitable networks.

Figure 6:
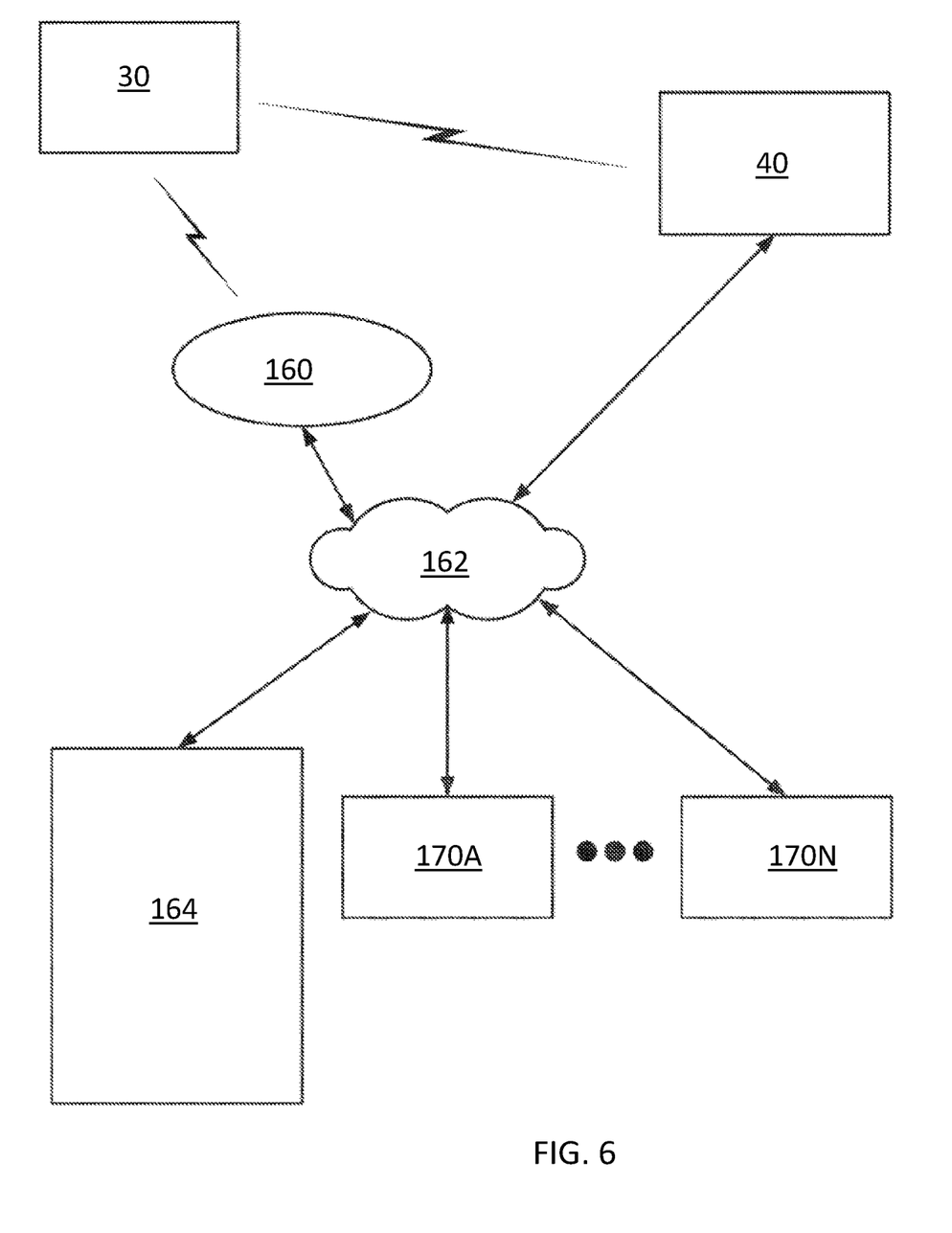
FIG. 6 is a schematic functional diagram illustrating communication of an implantable infusion device with one or more external devices.

For example, FIG. 6 illustrates an example system that includes an access point 160, a network 162, external computing devices, such as a server 164, and one or more other computing devices 170A-170N, which may be coupled to one or both of the implantable infusion device 30 and the patient personal device 40 via network 162. In this example, the implantable infusion device 30 may use communication circuitry to communicate with patient personal device 40 via a first wireless connection, and to communicate with an access point 160 via a second wireless connection. In the example of FIG. 6, access point 160, patient personal device 40, server 164, and computing devices 170A-170N are interconnected and may communicate with each other through network 162.

Access point 160 may comprise a device that connects to network 162 via any of a variety of connections, such as telephone dial-up, digital subscriber line (DSL), or cable modem, or other suitable connections. In other examples, access point 160 may be coupled to network 162 through different forms of connections, including wired or wireless connections. In some examples, access point 160 may be a user device, such as a tablet or smartphone, that may be co-located with the subject. The implantable infusion device 30 may be configured to transmit data, such as reservoir fill state, to patient personal device 40. In addition, access point 160 may interrogate the implantable infusion device 30, such as periodically or in response to a command from a subject, a clinician, or network 162, in order to retrieve information input by the subject (e.g., through a patient programmer device), device parameters, or other information stored in memory of implantable infusion device 30. Access point 160 may then communicate the retrieved data to server 164 via network 162.

The server 164 may be configured to provide a secure storage site for data collected from the implantable infusion device 30 or the patient personal device 40. In some cases, server 164 may assemble data in web pages or other documents for viewing by trained professionals, such as clinicians, via computing devices 170A-170N. One or more aspects of the illustrated system of FIG. 6 may be implemented with general network technology and functionality, which may include or be similar to that provided by the Medtronic Care Link® Network developed by Medtronic plc, of Dublin, Ireland.

Figure 7:
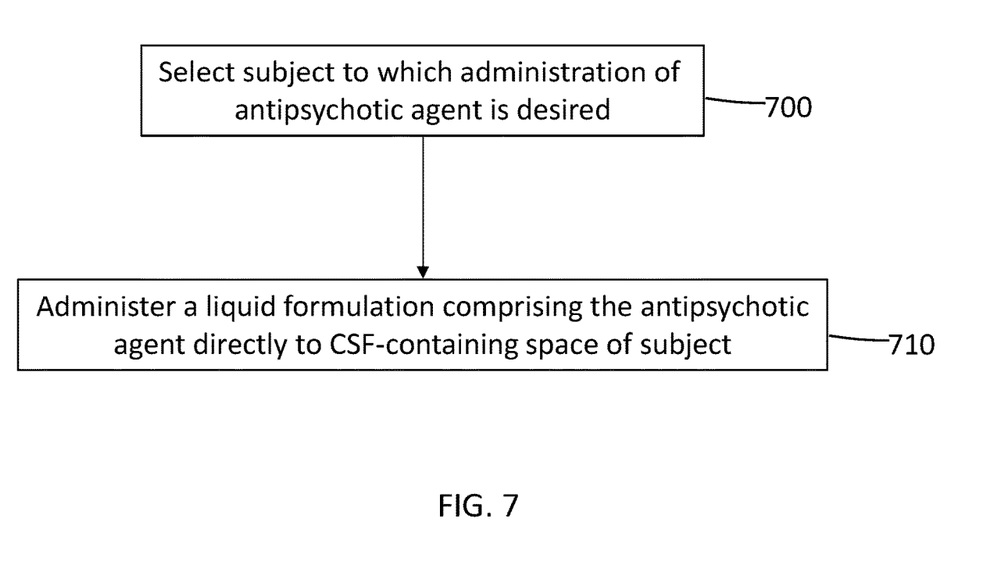
FIG. 7 is a flow chart illustrating a method according to an embodiment of the present disclosure.

Referring now to FIG. 7, a flow diagram illustrating a method according to the present disclosure is shown. The method includes selecting a subject to which administration of an antipsychotic agent is desired (700) and administering a liquid formulation comprising the antipsychotic agent directly to a CSF-containing space of the subject (710). The liquid formulation is preferably administered at a rate that is suitable to achieve broad distribution within the CSF. For example, the liquid formulation may be administered at a rate of 500 microliters per hour or less. The liquid formulation is preferably administered at a rate and duration suitable to achieve a therapeutically effective concentration of the antipsychotic agent in the CSF. For example, the liquid formulation may be administered at a rate of 500 microliters per hour or less for one or more days, one or more weeks, or one or more months.

Selecting a subject to which administration of the antipsychotic agent is desired (700) may be done in any suitable manner. For example, a heath care provider may diagnose the subject as suffering from a disease for with administration of an antipsychotic is warranted. Such diseases include those for which psychosis is a symptom. In some embodiments, the subject may be diagnosed as suffering from schizophrenia, bipolar disorder, or major neurocognitive disorder. The major neurocognitive disorder may be associated with Alzheimer's disease.

Below there is provided a non-exhaustive list of non-limiting examples of the present disclosure. Any one or more of the features of these examples may be combined with any one or more features of another example, embodiment, or aspect described herein.

Example Ex1: A method comprising (i) selecting a subject to which administration of an antipsychotic agent is desired; and (ii) administering a liquid formulation comprising the antipsychotic agent directly to cerebrospinal fluid (CSF)-containing space of the subject at a flow rate of less than 500 microliters per hour, wherein the liquid formulation is administered for a period of time sufficient to reach a therapeutically effective steady state concentration in CSF of a brain of the subject.

Example Ex2: The method according to Example Ex1, wherein the antipsychotic agent has a molecular weight in a range from 200 grams/mol to 600 grams/mol.

Example Ex3: The method according to Example Ex1 or Ex2, wherein the antipsychotic agent comprises a 5-hydroxytryptamine receptor 2a (5-HT2a) antagonist.

Example Ex4: The method according to Example Ex1 or Ex2, wherein the antipsychotic agent comprises a selective 5-HT2a antagonist.

Example Ex5: The method according to Example Ex1 or Ex2, wherein the antipsychotic agent comprises lumateperone tosylate.

Example Ex6: The method according to any one of Examples Ex1 to Ex5, wherein the liquid formulation is administered at a flow rate of less than 200 microliters per hour.

Example Ex7: The method according to any one of Examples Ex1 to Ex5, wherein the liquid formulation is administered at a flow rate of between about 4 microliters per hour and about 100 microliters per hour.

Example Ex8: The method according to any one of Examples Ex1 to Ex5, wherein the liquid formulation is administered at a flow rate of between about 2 microliters per hour and about 25 microliters per hour.

Example Ex9: The method according to any one of Examples Ex1 to Ex8, wherein the liquid formulation is delivered via a catheter having a delivery region placed in the CSF-containing space.

Example Ex10: The method according to Example Ex9, wherein the CSF-containing space is selected from the group consisting of lumbar intrathecal space, thoracic intrathecal space, and cervical intrathecal space.

Example Ex11: The method according to any one of Examples Ex1 to Ex10, further comprising administering the liquid formulation at a second slower rate for a period of time sufficient to reduce the concentration of the antipsychotic agent in the CSF.

Example Ex12: The method according to Example Ex11, wherein the liquid formulation is administered via a catheter, and wherein the second slower rate is sufficient to keep the catheter patent.

Example Ex13: The method according to any one of Examples Ex1 to Ex12, wherein the liquid formulation is delivered to the CSF-containing space by an implantable infusion device.

Example Ex14: The method according to any one of Examples Ex1 to Ex13, wherein the subject to which administration of the antipsychotic agent is desired is a subject suffering from one or more of schizophrenia, bipolar disorder, or major neurocognitive disorder.

Example Ex 15: The method according to Example Ex14, wherein the subject suffering from major neurocognitive disorder is a subject suffering from Alzheimer's disease.

Example Ex16: A system comprising: (i) a liquid formulation comprising an antipsychotic agent; and (ii) an implantable infusion device comprising (a) a reservoir configured to house the liquid formulation, (b) an outlet in fluid communication with the reservoir, (c) a drive mechanism configured to control the rate at which the liquid formulation is delivered to the outlet from the reservoir; and (d) control electronics operably coupled to the drive mechanism, wherein the electronics are programmed with instructions that cause the liquid formulation to be delivered from the reservoir to the outlet at a flow rate of less than 500 microliters per hour for a period of time sufficient to reach a therapeutically effective steady state concentration in a subject's cerebrospinal fluid (CSF) if the liquid is delivered to a CSF-containing space of a subject.

Example Ex17: The system according to Example Ex16, wherein instructions cause the liquid formulation to be administered at a flow rate of less than 200 microliters per hour.

Example Ex 18: The system according to Example Ex16, wherein instructions cause the liquid formulation to be administered at a flow rate of between about 4 microliters per hour and about 100 microliters per hour.

Example Ex19: The system according to Example Ex16, wherein instructions cause the liquid formulation to be administered at a flow rate of between about 2 microliters per hour and about 25 microliters per hour.

Example Ex20: The system according to any one of Examples Ex16 to Ex19, wherein the antipsychotic agent comprises a 5-HT2a antagonist.

For the purpose of the present description and of the appended claims, except where otherwise indicated, all numbers expressing amounts, quantities, percentages, and so forth, are to be understood as being modified in all instances by the term "about". Also, all ranges include the maximum and minimum points disclosed and include any intermediate ranges therein, which may or may not be specifically enumerated herein. In this context, therefore, a number A is understood as A±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Thus, embodiments of ADMINISTRATION OF ANTIPSYCHOTICS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
   selecting a subject to which administration of an antipsychotic agent is desired;
   administering a liquid formulation comprising the antipsychotic agent directly to cerebrospinal fluid (CSF)-containing space of the subject at a first flow rate of less than 500 microliters per hour, wherein the liquid formulation is administered for a period of time sufficient to reach a therapeutically effective steady state concentration in CSF of a brain of the subject, wherein the CSF-containing space is selected from the group consisting of lumbar intrathecal space, thoracic intrathecal space, and cervical intrathecal space; and wherein the antipsychotic agent comprises a 5-hydroxytryptamine receptor 2a (5-HT2a) antagonist.

2. The method according to claim 1, wherein the antipsychotic agent has a molecular weight in a range from 200 grams/mol to 600 grams/mol.

3. The method according to claim 1, wherein the antipsychotic agent comprises a selective 5-HT2a antagonist.

4. The method according to claim 1, wherein the antipsychotic agent comprises lumateperone tosylate.

5. The method according to claim 1, wherein the liquid formulation is administered at a flow rate of less than 200 microliters per hour.

6. The method according to claim 1, wherein the liquid formulation is administered at a flow rate of between about 4 microliters per hour and about 100 microliters per hour.

7. The method according to claim 1, wherein the liquid formulation is administered at a flow rate of between about 2 microliters per hour and about 25 microliters per hour.

8. The method according to claim 1, wherein the liquid formulation is delivered via a catheter having a delivery region placed in the CSF-containing space.

9. The method according to claim 1, further comprising administering the liquid formulation at a second flow rate for a period of time sufficient to reduce the concentration of the antipsychotic agent in the CSF, wherein the second flow rate is a flow rate lower than the first flow rate.

10. The method according to claim 9, wherein the liquid formulation is administered via a catheter, and wherein the second flow rate is sufficient to keep the catheter patent.

11. The method according to claim 1, wherein the liquid formulation is delivered to the CSF-containing space by an implantable infusion device.

12. The method according to claim 1, wherein the subject to which administration of the antipsychotic agent is desired is a subject suffering from one or more of schizophrenia, bipolar disorder, or major neurocognitive disorder.

13. The method according to claim 12, wherein the subject suffering from major neurocognitive disorder is a subject suffering from Alzheimer's disease.

14. A system comprising:

a liquid formulation comprising an antipsychotic agent; and an implantable infusion device comprising
  (i) a reservoir configured to house the liquid formulation,
  (ii) an outlet in fluid communication with the reservoir,
  (iii) a drive mechanism configured to control the rate at which the liquid formulation is delivered to the outlet from the reservoir; and
  (iv) control electronics operably coupled to the drive mechanism, wherein the electronics are programmed with instructions that cause the liquid formulation to be delivered from the reservoir to the outlet at a flow rate of less than 500 microliters per hour for a period of time sufficient to reach a therapeutically effective steady state concentration in a subject's cerebrospinal fluid (CSF) if the liquid is delivered to a CSF-containing space of a subject, wherein the CSF-containing space is lumbar intrathecal space, thoracic intrathecal space, or cervical intrathecal space, wherein the antipsychotic agent comprises a 5-HT2a antagonist.

15. The system according to claim 14, wherein instructions cause the liquid formulation to be administered at a flow rate of less than 200 microliters per hour.

16. The system according to claim 14, wherein instructions cause the liquid formulation to be administered at a flow rate of between about 4 microliters per hour and about 100 microliters per hour.

17. The system according to claim 14, wherein instructions cause the liquid formulation to be administered at a flow rate of between about 2 microliters per hour and about 25 microliters per hour.

18. The system according to claim 14, wherein the antipsychotic agent comprises a selective 5-HT2a antagonist.

19. The system according to claim 14, wherein the antipsychotic agent comprises lumateperone tosylate.

* * * * *